United States Patent [19]

McNary

[11] Patent Number: 5,899,200
[45] Date of Patent: May 4, 1999

[54] AEROSOL DISPENSING APPARATUS

[75] Inventor: Drew Haydn McNary, Brewster, N.Y.

[73] Assignee: Bespak plc, Norfolk, United Kingdom

[21] Appl. No.: 08/817,399

[22] PCT Filed: Jun. 23, 1995

[86] PCT No.: PCT/GB95/01473

§ 371 Date: Jun. 4, 1997

§ 102(e) Date: Jun. 4, 1997

[87] PCT Pub. No.: WO96/12661

PCT Pub. Date: May 2, 1996

[30] Foreign Application Priority Data

Oct. 25, 1994 [GB] United Kingdom .................. 9421482

[51] Int. Cl.$^6$ ................................................ A61M 11/00
[52] U.S. Cl. .................. 128/200.14; 128/200.23
[58] Field of Search ................ 128/200.14, 200.23, 128/200.22, 203.12, 200.4, 912, 203.15, 203.23; 604/58

[56] References Cited

U.S. PATENT DOCUMENTS

| 3,255,928 | 6/1966 | Foster ............................. 222/153 |
| 4,291,688 | 9/1981 | Kistler . |
| 4,509,515 | 4/1985 | Altounyan et al. .............. 128/200.23 |

FOREIGN PATENT DOCUMENTS

| 0052990 | 2/1982 | European Pat. Off. .......... 128/200.14 |
| 0201655 | 11/1986 | European Pat. Off. .......... 128/200.14 |
| 858959 | 1/1961 | United Kingdom ............. 128/200.14 |
| 2272162 | 11/1994 | United Kingdom ............. 128/203.12 |

Primary Examiner—John G. Weiss
Assistant Examiner—Charles W. Anderson
Attorney, Agent, or Firm—Smith, Gambrell & Russell, LLP; Beveridge, DeGrandi, Weilacher & Young Intellectual Property Group

[57] ABSTRACT

A dispensing apparatus for use with a pressurized dispensing container dispenses an aerosol spray. The dispensing apparatus includes a housing defining a tubular body that receives, in use, the pressurized dispensing container. A tubular mouthpiece projects laterally from the body, the mouthpiece having a tubular lip portion defining an outlet through which the aerosol spray is inhalable. A removable cap engages the mouthpiece to overlay the lip portion and close the outlet. A strap connects the cap to the body so that the cap is maintained with the housing when it is disengaged from the mouthpiece. The cap includes a tubular portion with an internal surface that conforms with an external surface of the lip portion. Movement of the cap into and out of the engaged position is accompanied by co-axial relative movement of the cap and the lip portion. The strap includes a web of plastic material having formed therein a plurality of transverse grooves defining fold lines about which the web folds in a bellows formation to accommodate extension and retraction of the strap during axial movement of the cap.

14 Claims, 8 Drawing Sheets

FIG. 1.

AEROSOL DISPENSING APPARATUS

This invention relates to a dispensing apparatus for use with a pressurized dispensing container operable to dispense an aerosol spray. Such containers typically comprise a valve having an actuating stem through which product is dispensed under pressure when the stem is moved relative to the container. A dispensing apparatus is typically therefore provided to receive the stem in a socket defining a spray nozzle such that the apparatus constitutes an actuator, the container being displaceable in a reciprocating manner relative to the apparatus in use to cause actuation resulting in an aerosol spray being dispensed.

Such apparatus typically comprises a housing having a tubular body receiving the container and a tubular mouth piece projecting laterally from one end of the body to define an outlet through which spray is dispensed, the other end of the body being open such that the container is accessible for applying finger pressure to displace the container. A user presents to his mouth a lip portion of the mouth piece during oral inhalation, and it is therefore desirable for the lip portion to be kept free from contamination between uses by means of a removable cap which also serves to close the mouth piece against the ingress of debris.

It has been proposed for such caps to be retained captive relative to the housing by means of a flexible strap secured at one end to the housing in order to prevent loss of the cap and to prevent accidental swallowing of the cap, the strap being of sufficient length to allow the cap to be moved into close proximity with the lip portion, and the cap being received as a snap fit onto the lip portion so as to close the outlet.

A disadvantage of such an arrangement is that the surface area of the lip portion likely to be coming into contact with the user's mouth is only partially overlaid by the cap when secured to the mouth piece thereby leaving the lip portion susceptible to contamination by handling and storage prior to use.

According to the present invention there is disclosed a dispensing apparatus for use with a pressurized dispensing container operable to dispense an aerosol spray, the apparatus comprising a housing defining a tubular body receiving in use the container and a tubular mouth piece projecting laterally from the body, the mouth piece having a tubular lip portion defining an outlet through which the aerosol spray is inhalable in use, a removable cap engageable with the mouth piece in an engaged position to overlay the lip portion and close the outlet, and a strap connecting the cap to the body whereby the cap is held captive relative to the housing when disengaged from the mouth piece, wherein the cap comprises a tubular portion having an internal surface conformal with the external surface of the lip portion whereby movement of the cap into and out of the engaged position is accompanied by co-axial relative movement of the cap and the lip portion and wherein the strap is of at least sufficient length to accommodate the axial movement of the cap relative to the body.

An advantage of such an arrangement is that the cap in the engaged portion overlays entirely the surface area of the lip portion likely to be touched by the user's mouth in use thereby providing improved hygiene.

Preferably the strap comprises a web of plastic material having formed therein a plurality of transverse grooves defining fold lines about which the web is foldable in bellows formation to accommodate extension and retraction of the strap during the axial movement of the cap.

An advantage of such an arrangement is that the cap is securely retained relative to the body by the web which is substantially inextensible beyond its unfolded length, the web being foldable into a plicated form in which movement of the cap into the engaged position is accommodated.

Preferably the strap is secured to the body so as to extend tangentially relative to a tubular side wall of the body.

An advantage of this arrangement is that the strap and cap do not obstruct the end wall of the housing which can then be engaged by the user's thumb or finger when presenting the housing for oral inhalation.

Preferred embodiments of the present invention will now be described by way of example only and with reference to the accompanying drawings of which.

Figure 1:
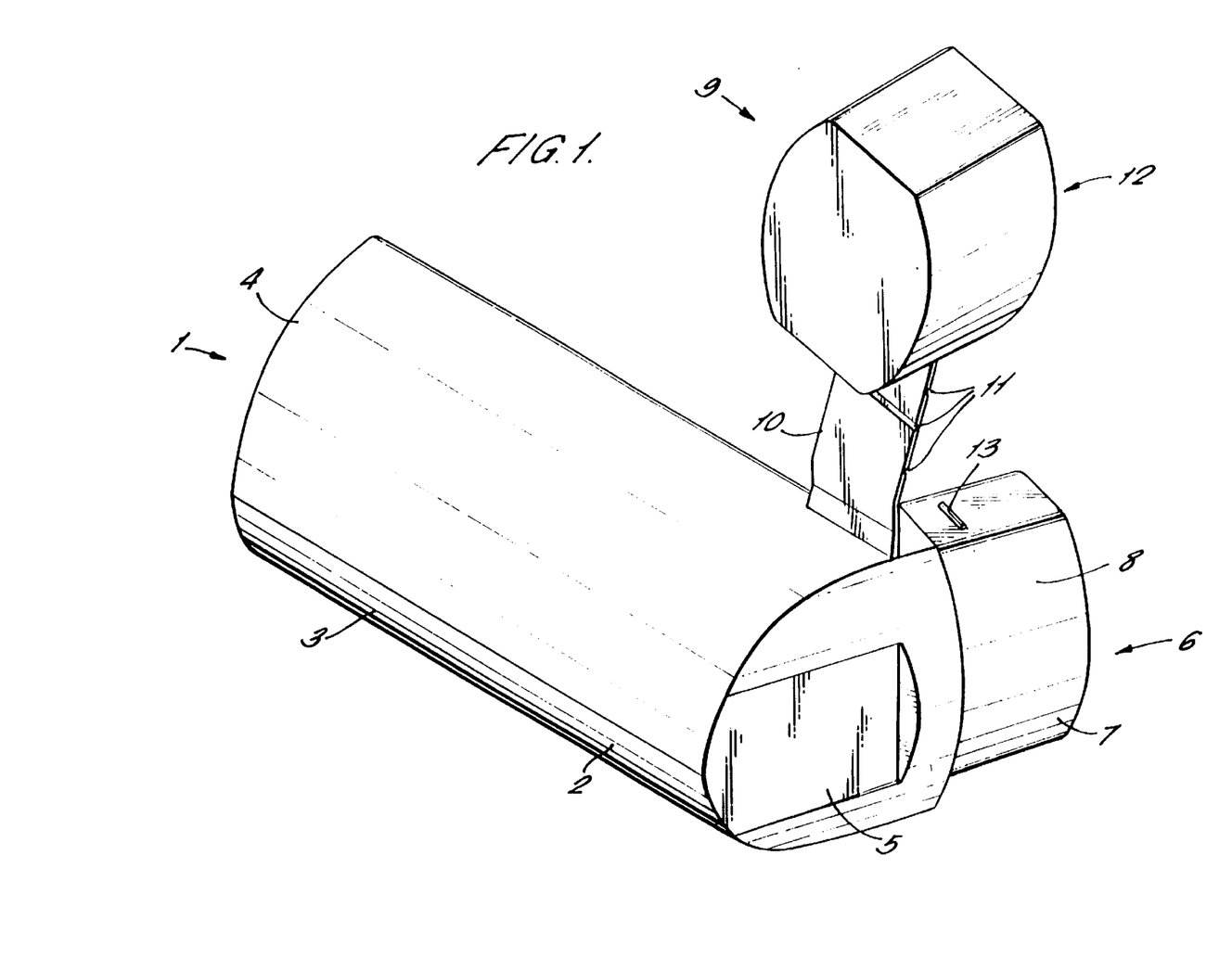
FIG. 1 is a perspective view of an apparatus having an integrally formed strap with the cap disengaged from the mouth piece.
Figure 2:
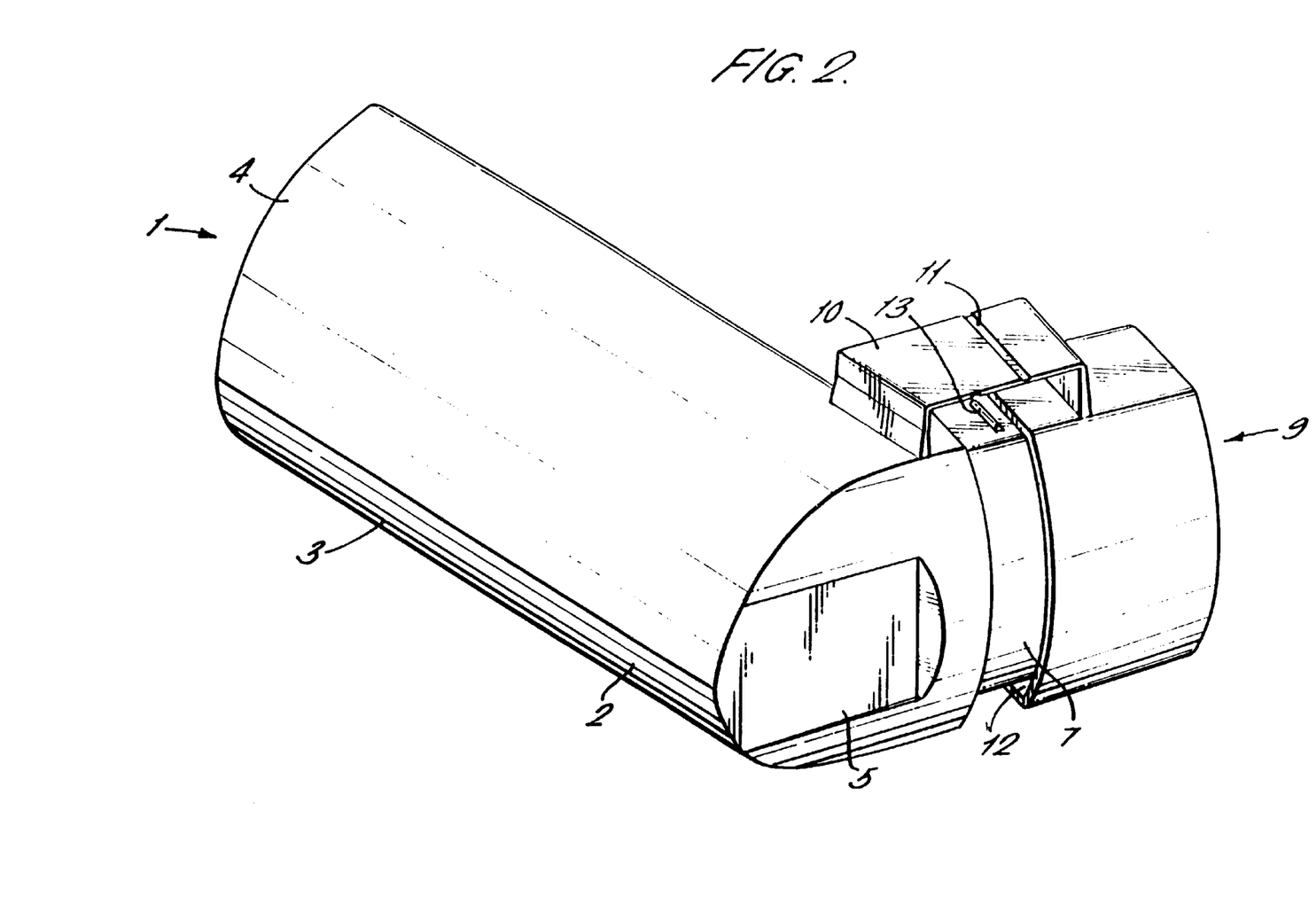
FIG. 2 is a perspective view of the apparatus of FIG. 1 showing the cap in co-axial alignment with the mouth piece immediately prior to movement of the cap into the engaged position on the mouth piece.

FIG. 1 shows an apparatus 1 comprising a housing 2 consisting of a tubular body 3 having a tubular side wall and an open end 4.

The body 3 is closed at its opposite end by an end wall 5 and a tubular mouth piece 6 projects laterally of the body at a location immediately adjacent the end wall.

The mouth piece 6 has a tubular lip portion 7 having an external surface S which in use is presented to the lips of a user wishing to inhale orally via the mouth piece an aerosol spray generated from a pressurized dispensing container (not shown) normally received within the body 3.

The apparatus 1 further comprises a cap 9 which is connected to the body 3 by a strap 10 formed of a then web of plastic material, the housing 2, cap 9 and strap 10 being unitarily formed of plastic material. The strap 10 is formed with a series of transverse grooves 11 defining fold lines about which the web is foldable in bellows formation as illustrated in FIG. 3.

Figure 3:
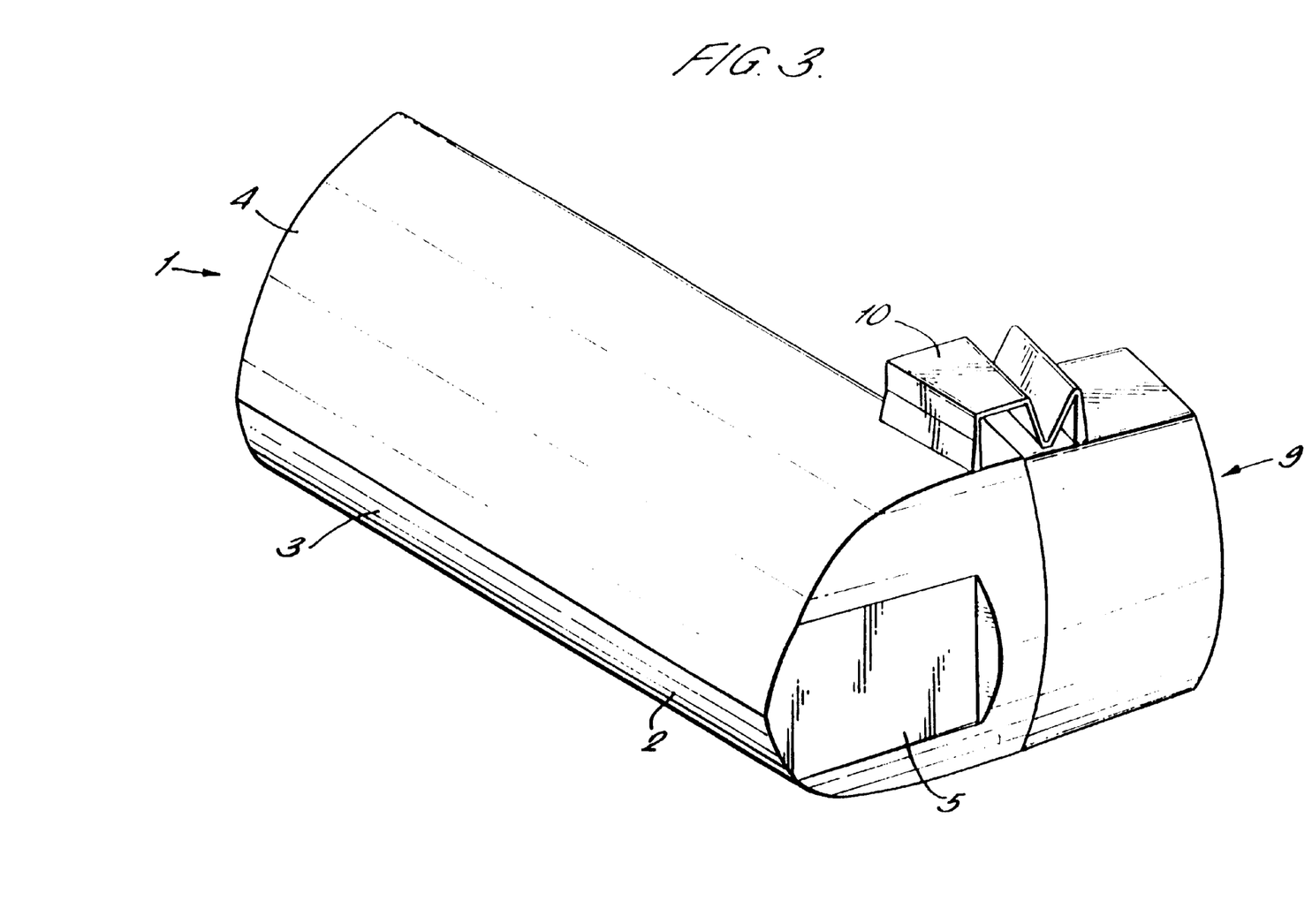
FIG. 3 is a perspective view of the apparatus of the preceding Figures showing the cap in the engaged position.

The cap 9 slidingly fits onto the lip portion 7 such that an internal surface 12 of the cap totally overlays the external surface S of the lip portion when the cap is moved into an engaged position as shown in FIG. 3 in which it is engaged with the mouth piece 6.

The lip portion 7 and the cap 9 are provided with cooperating snap fit connectors which include a detent 13, as shown in FIG. 1, projecting from the lip portion in a co-operating relationship with a groove (not shown) formed in the internal surface 12 of the cap 9.

As shown in FIG. 1, the cap is movable when disengaged from the mouth piece 6 into a lateral position in which it lies at a location which is offset from the axial extent of the body 2 and from the axial extent of the mouth piece 6 by a distance determined by the extended length of the strap 10.

In this lateral position, the user is able to grip the housing without interference from the presence of the cap and strap, the user typically resting a thumb against the end wall 5 and an index finger around the barrel shaped body 3.

In order to move the cap from this lateral position of FIG. 1 into the engaged position of FIG. 3 it is necessary to move the cap away from the body 3 into co-axial alignment with the mouth piece at a position in which the cap extends beyond the axial extent of the lip portion 7. The maximum extended length of the strap 10 must correspond at least to this configuration. Movement of the cap into the engaged position then proceeds by pushing the cap towards the body 3 in sliding relationship relative to the lip portion 7 until the detent 13 effects a snap fit connection and the cap rests in the fully engaged position shown in FIG. 3 in which the entire external surface S of the lip portion 7 is overlaid.

In the engaged position of FIG. 3 it is seen that the strap 10 is plicated into a shortened length in a bellows like manner.

Figure 6:
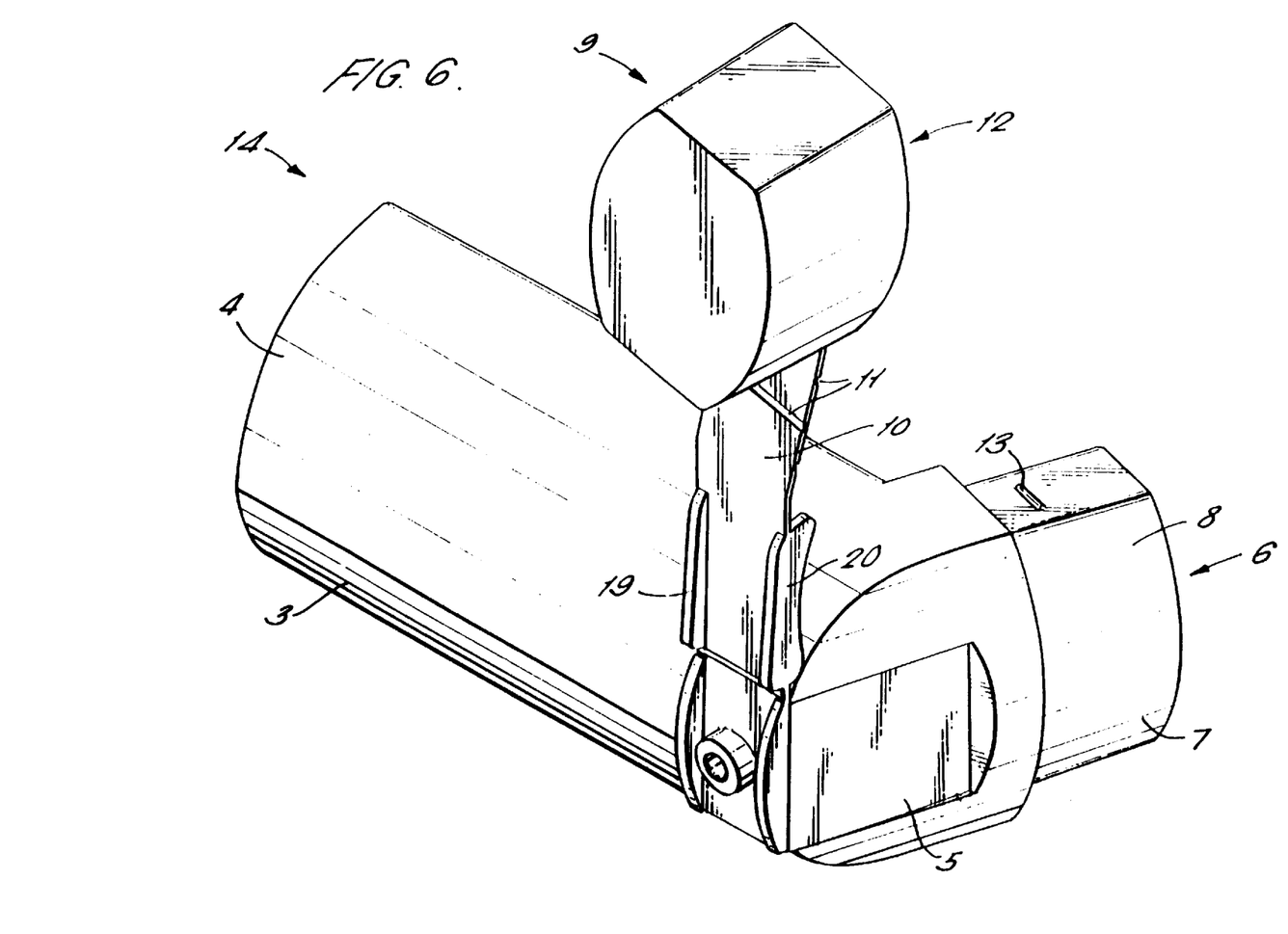
FIG. 6 is a perspective view of the alternative apparatus comprising the housing and cap of FIGS. 4 and 5, shown in a position in which the cap is disengaged from the mouth piece.
Figure 7:
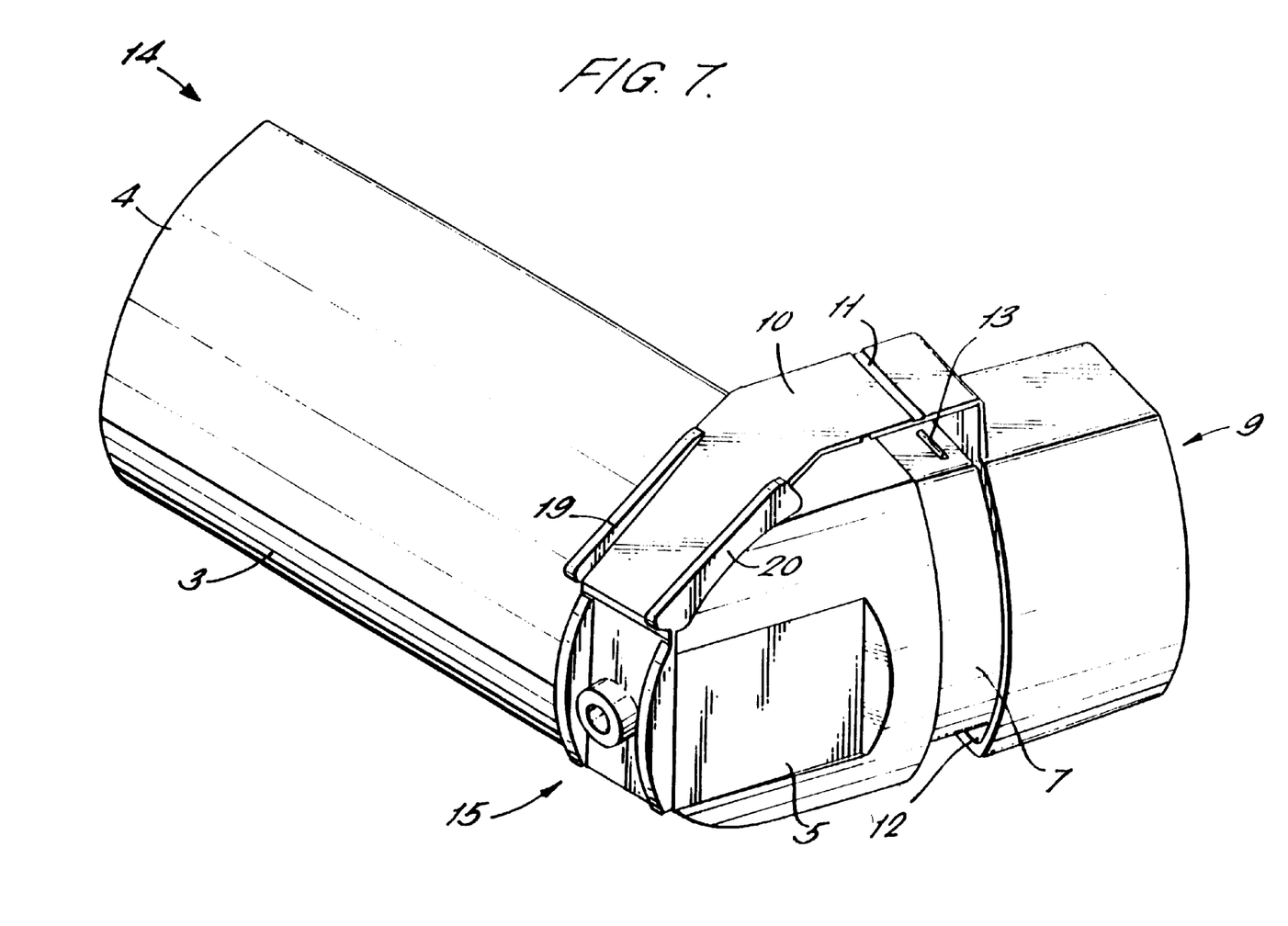
FIG. 7 is a perspective view of the apparatus of FIG. 6 showing the cap at an intermediate position in which the cap is axially displaced from the engaged position.
Figure 8:
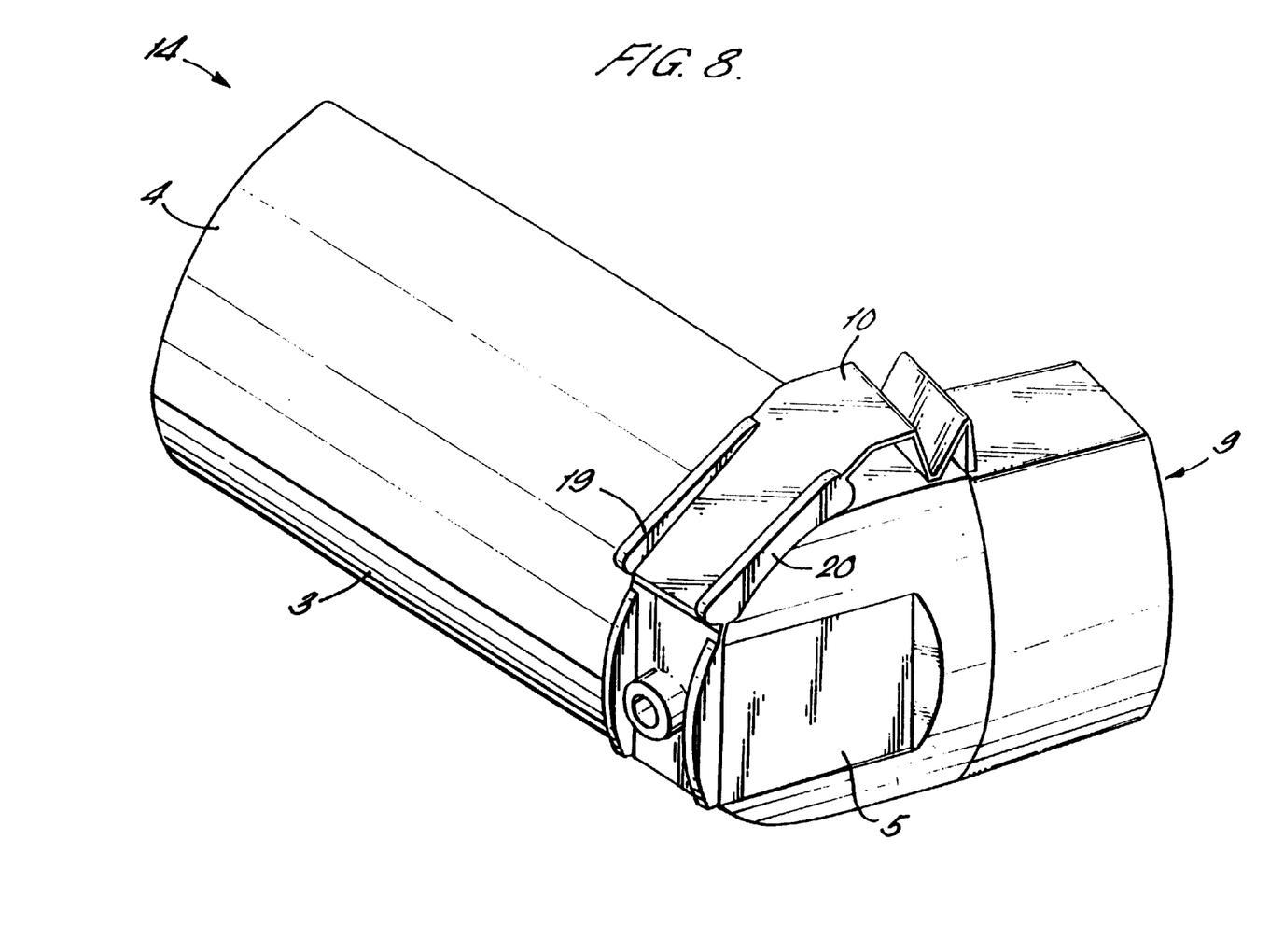
FIG. 8 is a perspective view of the apparatus of FIGS. 6 and 7 showing the cap in the engaged position.

An alternative apparatus 14 is shown in FIGS. 6, 7 and 8 and will now be described using corresponding reference numerals to those of preceding figures where appropriate for corresponding elements.

The alternative apparatus 14 similarly includes a body 3, lip portion 7, cap 9 and strap 10, but the strap is secured to the body by means of co-operating stud fastener formations 15.

Figure 4:
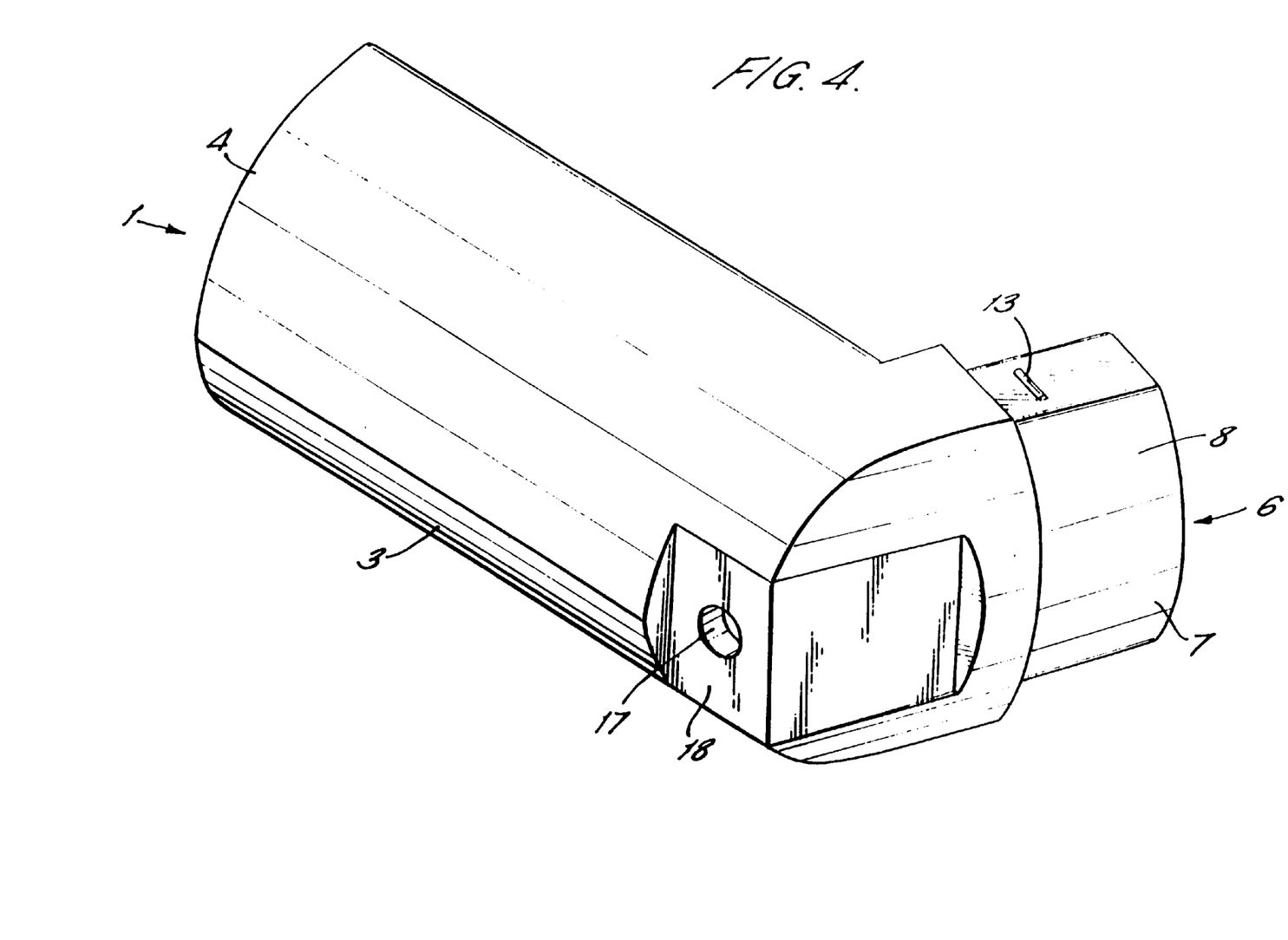
FIG. 4 is a perspective view of a housing of an alternative apparatus.
Figure 5:
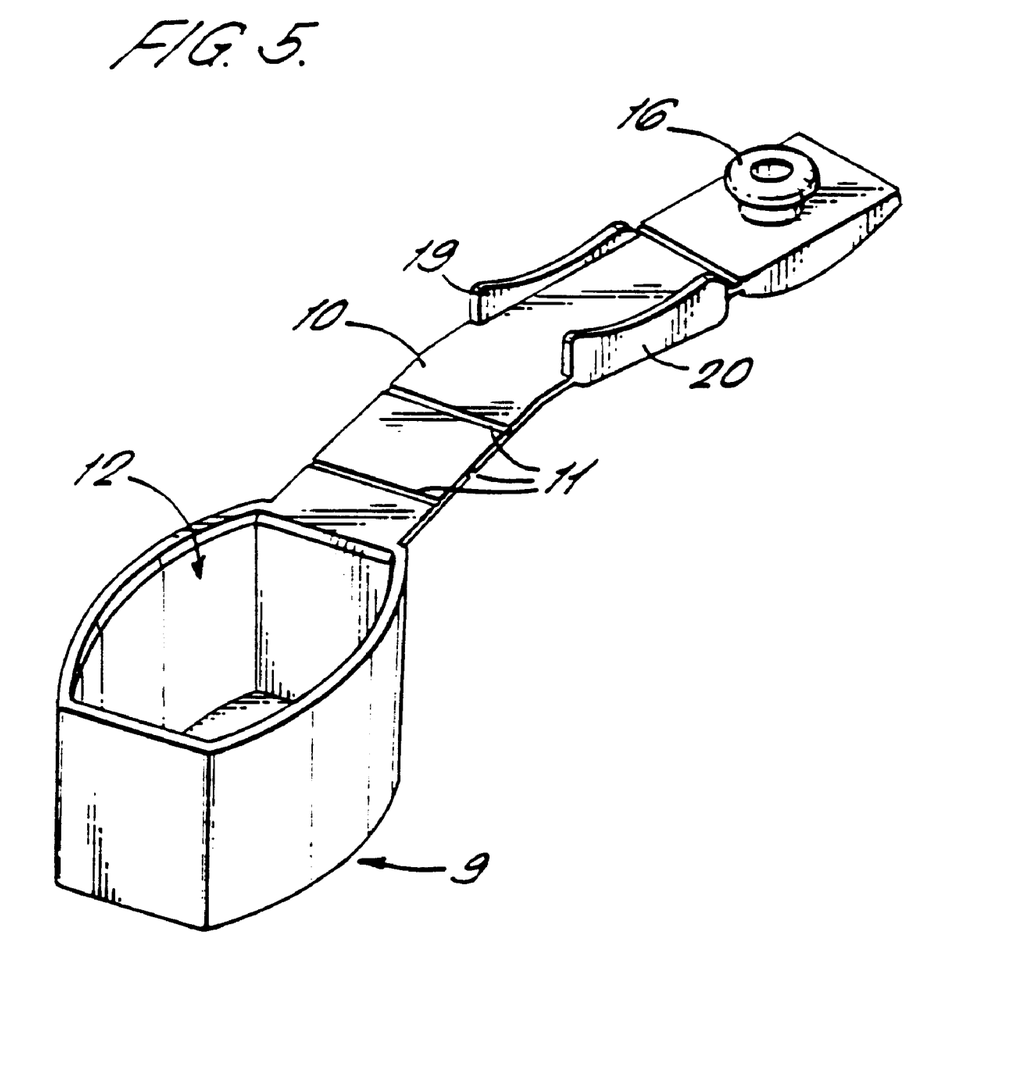
FIG. 5 is a perspective view of a cap and strap co-operable with the housing of FIG. 4.

The stud fastener formations 15 comprise a stud 16 formed integrally with the strap as shown in FIG. 5 and received as a push fit into a socket 17 as shown in FIG. 4. As shown in FIG. 4, the socket 17 is formed in a bevelled surface 18 of the body 3 such that the strap is constrained to extend in a direction tangential to a circumference of the body, the strap thereby being able to extend in an arcuate configuration around a partial circumference of the body when moved into the engaged position as shown in FIG. 8.

The strap 10 is further provided with stand off projections 19 and 20 which project from respective side edges of the strap and at right angles to the plane of the strap so as to provide a stand off separation between the strap and the body 3 at a location from which the strap extends tangentially from the tubular side wall of the body. As shown in FIG. 8, this stand off facilitates the plication of the strap in the vicinity of the grooves 11 when the length of the strap is shortened as in the engaged position shown in FIG. 8.

The alternative apparatus 14 may be modified to form stud fastener formations in which a stud projects integrally from the body 3 and is received in a socket formed in an end portion of the strap.

I claim:

1. A dispensing apparatus for use with a pressurized dispensing container operable to dispense an aerosol spray, the apparatus comprising:

a housing defining a tubular body for receiving in use the container, the housing further defining a tubular mouth piece projecting laterally from the body, the mouth piece having a tubular lip portion defining an outlet through which the aerosol spray is inhalable in use, a removable cap engageable with the mouth piece in an engaged position to overlay the lip portion and close the outlet, and a strap connecting the cap to the body such that the cap is held captive relative to the housing when disengaged from the mouth piece, wherein the cap includes a tubular portion having an internal surface conformal with an external surface of the lip portion, wherein movement of the cap into and out of the engaged position is accompanied by co-axial relative movement of the cap and the lip portion, wherein the strap is of at least sufficient length to accommodate the axial movement of the cap relative to the body, and wherein the strap includes a web of plastic material having formed therein a plurality of transverse grooves defining fold lines about which the web folds in a bellows formation to accommodate extension and retraction of the strap during the axial movement of the cap.

2. A dispensing apparatus as claimed in claim 1, wherein the strap is secured to the body so as to extend tangentially relative to a tubular side wall of the body.

3. A dispensing apparatus as claimed in claim 2, wherein the strap includes one or more stand off projections that provide a stand off separation between the strap and the body at a location at which the strap extends tangentially relative to the body.

4. A dispensing apparatus as claimed in claim 3, wherein the strap is connected to the body by means of stud fastener formations, which include a stud formed on one of the strap and the body, and a socket for receiving the stud, the socket being located on the other of the strap and the body.

5. A dispensing apparatus as claimed in claim 3, wherein the cap, the strap and the body are formed unitarily from a plastic material.

6. A dispensing apparatus as claimed in claim 3, wherein the strap is connected to the body such that, when the cap is disengaged from the mouth piece, the cap and strap are located at a lateral position relative to the body, in which position the strap extends substantially orthogonally relative to tubular axes of both the body and the mouth piece.

7. A dispensing apparatus as claimed in claim 2, wherein the strap is connected to the body by means of stud fastener formations, which include a stud formed on one of the strap and the body, and a socket for receiving the stud, the socket being located on the other of the strap and the body.

8. A dispensing apparatus as claimed in claim 2, wherein the cap, the strap and the body are formed unitarily from a plastic material.

9. A dispensing apparatus as claimed in claim 2, wherein the strap is connected to the body such that, when the cap is disengaged from the mouth piece, the cap and strap are located at a lateral position relative to the body, in which position the strap extends substantially orthogonally relative to tubular axes of both the body and the mouth piece.

10. A dispensing apparatus as claimed in claim 1, wherein the strap is connected to the body by means of stud fastener formations, which include a stud formed on one of the strap and the body, and a socket for receiving the stud, the socket being located on the other of the strap and the body.

11. A dispensing apparatus as claimed in claim 10, wherein the strap is connected to the body such that, when the cap is disengaged from the mouth piece, the cap and strap are located at a lateral position relative to the body, in which position the strap extends substantially orthogonally relative to tubular axes of both the body and the mouth piece.

12. A dispensing apparatus as claimed in claim 1, wherein the cap, the strap and the body are formed unitarily from a plastic material.

13. A dispensing apparatus as claimed in claim 12, wherein the strap is connected to the body such that, when the cap is disengaged from the mouth piece, the cap and strap are located at a lateral position relative to the body, in which position the strap extends substantially orthogonally relative to tubular axes of both the body and the mouth piece.

14. A dispensing apparatus as claimed in claim 1, wherein the strap is connected to the body such that, when the cap is disengaged from the mouth piece, the cap and strap are located at a lateral position relative to the body, in which position the strap extends substantially orthogonally relative to tubular axes of both the body and the mouth piece.

* * * * *